(12) United States Patent
Kantelhardt

(10) Patent No.: US 9,339,300 B2
(45) Date of Patent: May 17, 2016

(54) DYNAMIC STABILIZING DEVICE FOR BONES

(71) Applicant: Sven Kantelhardt, Mainz (DE)

(72) Inventor: Sven Kantelhardt, Mainz (DE)

(73) Assignee: University of Medical Center of Johannes Guten University Mainz, Mainz (DE)

( * ) Notice: Subject to any disclaimer, the term of this patent is extended or adjusted under 35 U.S.C. 154(b) by 613 days.

(21) Appl. No.: 13/669,325

(22) Filed: Nov. 5, 2012

(65) Prior Publication Data

US 2014/0128920 A1 May 8, 2014

(51) Int. Cl.
*A61B 17/70* (2006.01)

(52) U.S. Cl.
CPC ......... *A61B 17/7031* (2013.01); *A61B 17/7014* (2013.01); *A61B 17/7016* (2013.01)

(58) Field of Classification Search
CPC ........... A61B 17/7001; A61B 17/7002; A61B 17/701; A61B 17/7011; A61B 17/7013; A61B 17/7019; A61B 17/702; A61B 17/7025; A61B 17/7026; A61B 17/7028; A61B 17/7029; A61B 17/7031; A61B 17/7032; A61B 17/7034; A61B 17/7035; A61B 17/7037; A61B 17/7038; A61B 17/7041; A61B 17/7043; A61B 17/7046
See application file for complete search history.

(56) References Cited

U.S. PATENT DOCUMENTS

| | | | |
|---|---|---|---|
| 2003/0093078 A1* | 5/2003 | Ritland | A61B 17/7007 606/900 |
| 2005/0085814 A1* | 4/2005 | Sherman | A61B 17/7026 606/257 |
| 2006/0189983 A1* | 8/2006 | Fallin | A61B 17/7007 606/250 |
| 2007/0055244 A1* | 3/2007 | Jackson | A61B 17/7028 606/86 A |
| 2007/0100341 A1* | 5/2007 | Reglos | A61B 17/7004 606/86 A |
| 2007/0167948 A1* | 7/2007 | Abdou | A61B 17/7005 606/86 A |
| 2007/0203446 A1* | 8/2007 | Biedermann | A61B 17/7028 604/11 |
| 2007/0233085 A1* | 10/2007 | Biedermann | A61B 17/7031 606/86 A |
| 2007/0270860 A1* | 11/2007 | Jackson | A61B 17/7008 606/326 |
| 2008/0021459 A1* | 1/2008 | Lim | A61B 17/702 606/279 |
| 2008/0039843 A1* | 2/2008 | Abdou | A61B 17/7005 606/255 |

(Continued)

*Primary Examiner* — Pedro Philogene
*Assistant Examiner* — Lynnsy Summitt
(74) *Attorney, Agent, or Firm* — Jennifer S. Stachniak

(57) ABSTRACT

A dynamic stabilizing device (1) for bones (3), in particular for vertebrae, includes two bone anchoring elements (2) spaced from one another, which are connectable via fastening elements (4) with at least one rod (5) that is at least partly elastic. The rod (5) has an adjustable device (7) for affecting its elasticity, which is adjustable before and/or after the implantation of the stabilizing device (1). The adjustable device (7) is formed, such that it changes the free length of an elastic section (11) of the rod (5). The adjustable device (7) includes a carriage that is displaceable over the rod (5), and the carriage (20) engages the rod (5) on a peripheral side at least partially.

13 Claims, 2 Drawing Sheets

(56) References Cited

U.S. PATENT DOCUMENTS

| | | | | |
|---|---|---|---|---|
| 2008/0045951 | A1* | 2/2008 | Fanger | A61B 17/7005 606/86 A |
| 2008/0065079 | A1* | 3/2008 | Bruneau | A61B 17/7004 606/62 |
| 2008/0177317 | A1* | 7/2008 | Jackson | A61B 17/7026 606/254 |
| 2008/0183213 | A1* | 7/2008 | Veldman | A61B 17/702 606/257 |
| 2008/0269904 | A1* | 10/2008 | Voorhies | A61B 17/7026 606/86 A |
| 2009/0088782 | A1* | 4/2009 | Moumene | A61B 17/7004 606/151 |
| 2009/0093820 | A1* | 4/2009 | Trieu | A61B 17/7004 606/103 |
| 2009/0234388 | A1* | 9/2009 | Patterson | A61B 17/7031 606/246 |
| 2009/0287251 | A1* | 11/2009 | Bae | A61B 17/7031 606/254 |
| 2009/0326582 | A1* | 12/2009 | Songer | A61B 17/702 606/255 |
| 2009/0326584 | A1* | 12/2009 | Slivka | A61B 17/7025 606/261 |
| 2010/0087858 | A1* | 4/2010 | Abdou | A61B 17/7005 606/246 |
| 2010/0087862 | A1* | 4/2010 | Biedermann | A61B 17/702 606/259 |
| 2010/0318130 | A1* | 12/2010 | Parlato | A61B 17/7028 606/254 |
| 2010/0331887 | A1* | 12/2010 | Jackson | A61B 17/7008 606/264 |
| 2011/0245873 | A1* | 10/2011 | Winslow | A61B 17/7005 606/254 |
| 2011/0251648 | A1* | 10/2011 | Fiechter | A61B 17/60 606/286 |
| 2012/0109207 | A1* | 5/2012 | Trieu | A61B 17/7002 606/254 |
| 2012/0310285 | A1* | 12/2012 | Zhao | A61B 17/7025 606/264 |
| 2013/0110171 | A1* | 5/2013 | Suh | A61B 17/7014 606/257 |
| 2013/0282061 | A1* | 10/2013 | Janice | A61B 17/702 606/246 |
| 2014/0025116 | A1* | 1/2014 | Wei | A61B 17/7019 606/255 |

\* cited by examiner

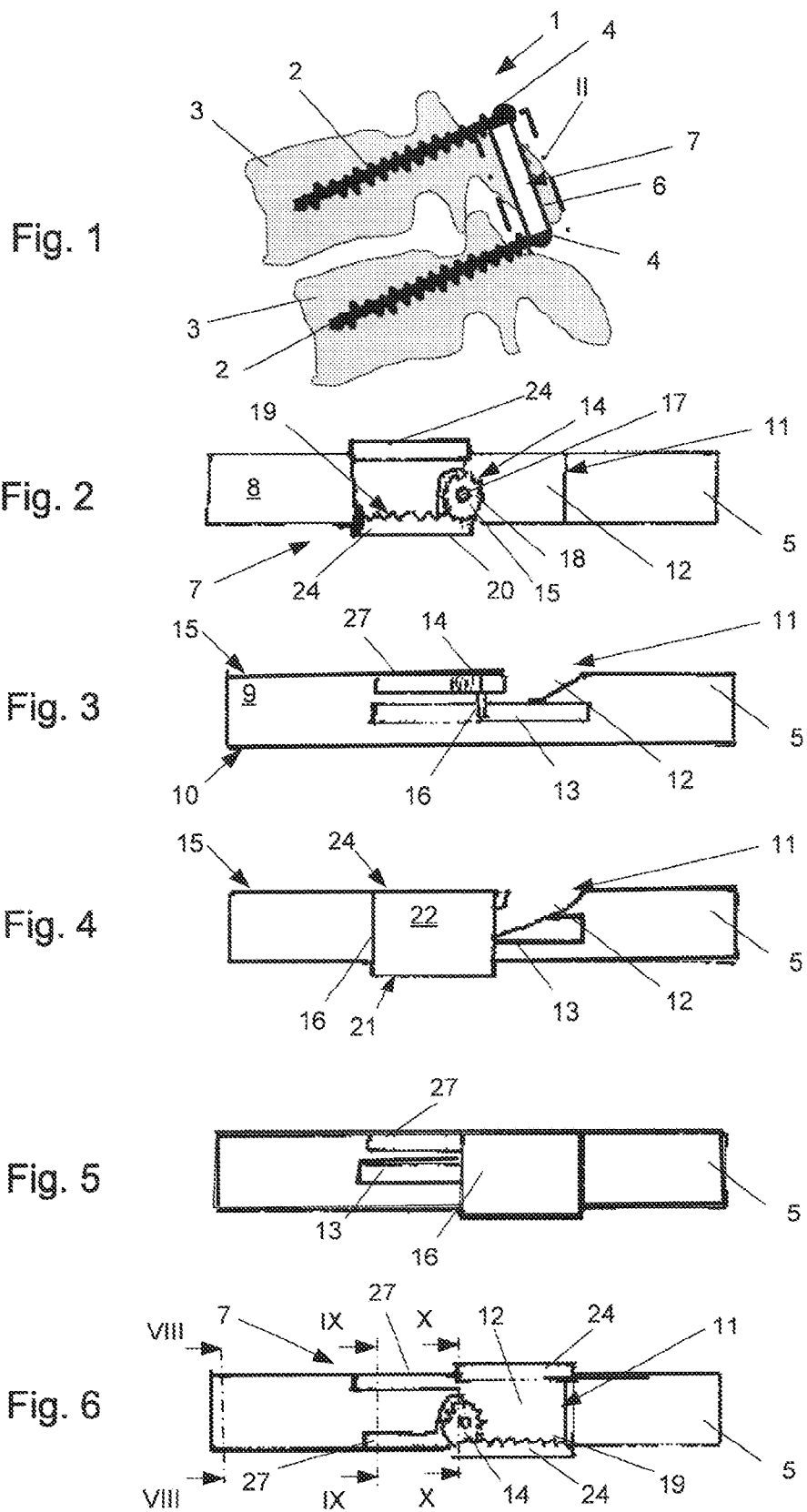

DYNAMIC STABILIZING DEVICE FOR BONES

The invention relates to a dynamic stabilizing device for bones, in particular for vertebrae, with two bone anchoring elements spaced from one another, which are connectable via fastening elements with at least one partially elastic rod.

In the frame of spinal column injuries (trauma), denegation and other illnesses (tumors, etc.), instabilities of the spinal column consistently occur. According to a classic method, in such cases a stabilizing of the affected spinal column segments takes place with pedicle screws behind tension band wiring of the rear column and placeholders in the intervertebral disc space for supporting the central column.

According to one further development, so called dynamic systems have been made available, which provide the bones a greater stimulus for healing or regeneration, since a completely rigid stabilization does not take place. Laboratory data shows a faster heading of the bones without a complete surgical fusion. With the dynamic systems for stabilizing of a spinal column segment, a flexible connecting rod is arranged between the pedicle screws. According to a further improved method, support of a damaged intervertebral disc takes place by the exclusive use of pedicle screws connected to one another by means of a flexible connecting rod. With these methods, the operative engagement and the change of the normal anatomy is substantially less than with earlier treatment methods. In addition, it is possible to combine the known techniques as "topping off" or "topping down", so that a damaged segment is combined with an adjacent segment which shows less intensive degeneration but is only dynamically stabilized. This also appears to be particularly sensible since with a fusion of a segment, the adjacent segment compensates for a loss in mobility and therefore, its load increases. For example, with a "topping off", the lower segment is provided with pedicle screws and place holders in the intervertebral dis, and the upper segment only with the dynamic screw-rod system.

A plurality of dynamic systems for stabilizing segments of the spinal column are known from this practice, which for example include flexible connecting rods made from polyetheretherketone (PEEK) or from titanium springs or substantially rigid connecting rods, which are attached with joints to the pedicle screws.

The known systems for dynamic stabilization are problematic in that a too "weak" adjustment, in particular a comparatively flexible connecting rod, is not helpful in view of stabilization and leads to an adjustment that is too "hard", that is, for example leads to a more rigid connecting rod, to loosening of the pedicle screws or a breakage of the system.

An optical rigidity of the system, preferably of the connecting rod, is not achievable for all patients, since heavier patients with a hard bones certainly required a more rigid system for effective support of the affected segments that a patient with osteoporosis, which require a relative "weak" adjustment, that is a flexible system, in order to prevent loosening of the pedicle screws in the bone. In addition, it should therefore be calculated that the "optimal rigidity" of the system changes during the course of the life of a patient, only with increasing osteoporosis or weight, but also as a function of the development of illnesses and the integration of the pedicle screws. Thus, for example, directly after implantation, it is possible that a relatively flexible, that is weakly installed system is favorable in order to facility the integration, while with increasing degeneration and under certain circumstances of a beginning spontaneous fusion of the vertebral disc, an increasingly "harder" adjustment is necessary.

DE 10 2006 003 374 A1 discloses a flexible connecting element for the implantation in human or animal bodies, in particular for stabilization of the spinal column, with a rod, which has at least one flexible region and at least two connecting regions for fastening of the elements to be connected. At least in one part of the flexible region of the rod, a flexible element or stabilizing element is provided, which is arranged outside of the rod cross section and is connected axially, non-displaceably at least at one position with the rod. This dynamic stabilizing system makes possible the combination of different module components before or during implantation. An individual adjustment of the rigidity or preliminary tension of the implant is not provided.

In addition, DE 102 36 691 A1 shows a dynamic stabilizing device for bones, in particular for vertebrae, with at least a first and a second bone anchoring element, with, respectively, a first section to be anchored in a bone and a second section to be connected with a rod, and a rod connecting the bone anchoring elements, whereby the bone anchoring elements are connectable with the rod selectively fixedly or displaceably in the direction of the rod axis. Between the bone anchoring elements, an elastic element that is pretensioned in the direction of the rod axis is provided. The elastic element affects in a first line a more or less great traction effect, in the sense of the vertebral bodies pressing against one another and has no effect on the flexibility or elasticity of the rod between the anchoring screws; that is the possible bending under load of the rod is not affected by the elastic element.

The present invention is based on the object of producing a dynamic stabilizing device for bones of the above-mentioned type, which is adaptable individually to patient-specific requirements and thereby, is manageable in a simple manner.

According to the present invention, the object is solved by the feature of claim 1, 14, or 15.

The dependent claims represent advantageous embodiments of the invention.

A dynamic stabilizing device for bones, in particular for vertebrae, includes two bone anchoring elements that are spaced from one another, which are connectable via fastening elements with at least one sectionally elastic rod, whereby the rod has an adjustable device for affecting its elasticity.

The elastic rod, that is a rod that is automatically resettable from a deformed position into an original position, can be individually adapted to patient-specific needs by means of the continuously variably adjustable device, in that its elasticity can be changed. For example, the rod can be used in a "weak", that is relatively elastic placement or position with a patient with osteoporosis, whereby a relatively large elasticity preferably prevents a loosening of the bone anchoring elements, formed in particularly as pedicle screws, in the bone. With a patient with a hard bone and a relatively high weight, the device can be altered, such that the elasticity of the rod is reduced; that is a relative rigid system for effective support of the bones is provided. In this connection, the device can engaged in the interior of a hollow rod or on the outer circumference of a solid rod. It is contemplated that an element that is adjustable via an end-face adjustment screw is inserted in the interior of a rod, which more or less dips into the elastic region of the rod and thereby correspondingly stabilizes the rod. It also is possible to insert a spring element into the interior of the rod, which is pretensioned to a greater or lesser degree by corresponding adjustment screws. On the outside, a telescoping sleeve or the like can be provided, which more or less engages over the elastic region of the rod and thereby changes accordingly the elastic deformability of the rod.

Advantageously, the device is adjustable before and/or after the implantation of the stabilizing device. The continuously variable adjustability of the device after implantation is of particular interest, since based on a healing process or changed patient-related needs, a change of the elasticity of the rod is advantageous. The device can be placed during implantation, such that it is adjustable by means of magnetic force or after a small contact, in particular a puncture.

Advantageously, the device is embodied such that the free length of the elastic section of the rod is changed. If the elastic section has a relatively short free length, then the rod is adjusted to be "hard" or "strong"; if the elastic section is relatively long, then minimal forces for deformation of the rod are necessary and the rod is adjusted to be "weak".

In one embodiment, the device includes a carriage that is displaceable over the rod, the carriage engaging the rod at least partially on the peripheral side. The carriage is more or less moved over the elastic region of the rod, in order to change the elasticity of the rod. In this connection, the carriage operates like a rail supporting the rod in its elastic region.

For fine turning of the carriage, the device has an adjusting wheel for displacing the carriage, whereby the adjusting wheel is provided with a contact for a tool and/or is made from a magnetic material, in particular is rotatably mounted in the rod. The adjusting wheel, which for example is rotatable with a screwdriver, an Allen wrench or hexagonal key, which is known by the tradename Torx, acts upon the carriage to its continuous linear displacement relative to the rod in a force-fit or form-locking manner. When the adjusting wheel is made from a magnetic material, its rotation is made possible by means of magnetic force after implantation without a surgical contact. Advantageously, the adjusting wheel has toothing on at least a part of its outer circumferential, which cooperates with a corresponding toothed bar of the carriage displaceable relative to the adjusting wheel. The toothed bar, of course, can be an integral component of the carriage, whereby a toothing is incorporated in an edge region of the carriage.

According to a further embodiment, the rod has a sectional weakening for formation of its elastic section, which can be covered by the carriage. The reduction of the cross section need not be distributed uniformly over the circumference, but can be provided on one side or that the rod is asymmetrical. The narrowed cross section of the rod is directed toward the bone to be stabilized, in order to enable a desired motion in a specific direction.

The rod preferably has at least one guide groove extending parallel to its longitudinal axis, in which a guide nose of the displaceable carriage slidingly engages, whereby the guide groove preferably extends over the elastic section coverable by the carriage and has a length, such that the carriage releases the elastic section in one end position and in its other end position, covers the elastic section over its length. By means of the guide groove, the carriage is located in a defined position relative to the rod as well as to the adjusting wheel.

So that an ingrowth of the carriage after the implant is prevented and its displacement along the longitudinal axis of the rod is ensured, with the exception of projections for the attachment elements, the rod is covered with a coating made of plastic, whereby the coating in particular covers the device and the elastic section of the rod.

For a displacement of the carriage after the implantation by means of a tool engaged on the adjusting wheel, a free access for contact of the adjusting wheel for a tool is necessary, without substantial damage of the coating; thus, the coating has a conical bore on its circumferential side, which runs coaxially to the adjusting wheel. Advantageously, the coating is made from a silicon or polyetheretherketone (PEEK). Of course, the practitioner is aware of further biocompatible materials, which can find use with the present invention.

The rod is made from a titanium material or is embodied in the longitudinal direction in two parts, whereby one part is made from titanium material and the other part is made from plastic, in particular from a polyetheretherketone composite.

So that the carriage limits the rod in its elasticity, the carriage is made from titanium material, which preferably has a higher rigidity relative to the titanium material of the rod.

If the surgeon has available a modular system for a dynamic stabilizing device for bones, in particular for vertebrae, with two bone anchoring elements, fastening elements for connection of a rod with the bone anchoring elements and multiple robs with different elastic properties, then he can select the rods provided in the modular system whose elastic properties appear to be suitable for the characteristics of the patient to be treated. With a lightweight patient with osteoporosis, then, he uses a rod with a greater elasticity than with a heavy patient with solid bones.

It is to be understood that the features described above and in the following description are not to be limited to the respective combinations provided, but also are useable in other combinations. The frame of the invention is defined only by the claims.

BRIEF DESCRIPTION OF THE DRAWINGS

The invention will be described next with reference to two exemplary embodiments shown in the accompanying drawings. In the drawings:

FIG. 1 shows a schematic representation of a dynamic stabilizing device anchored in two bones;

FIG. 2 shows an enlarged partial representation of a detail II according to FIG. 1 from above with a carriage in a first end position;

FIG. 3 shows a partial representation of the stabilizing device of FIG. 1 from the side;

FIG. 4 shows a side view of the representation according to FIG. 1;

FIG. 5 shows a representation according to FIG. 3 with the carriage in a second end position;

FIG. 6 shows a plan view of the representation of FIG. 4;

Figure 7:
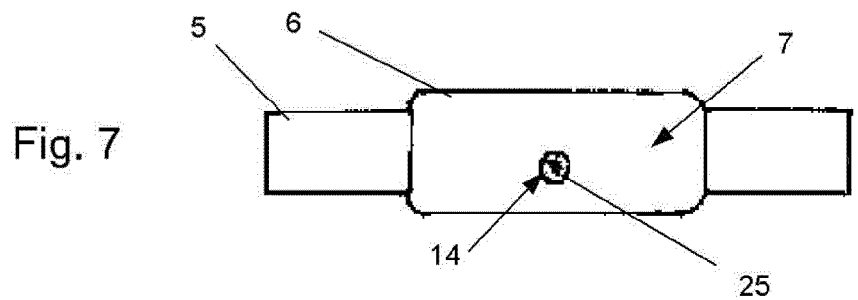
FIG. 7 shows a further representation of the detail II according to FIG. 1.
Figure 8:
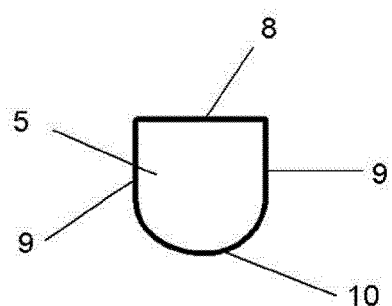
FIG. 8 shows a representation of a carriage along lines VII-VII of FIG. 5.
Figure 9:
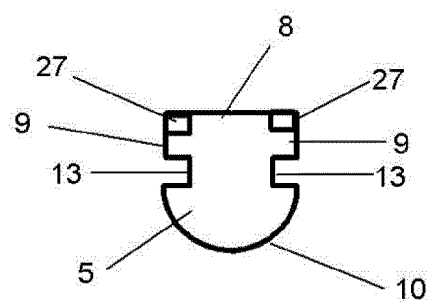
FIG. 9 shows a representation of a carriage along the line VIII-VIII of FIG. 5.
Figure 10:
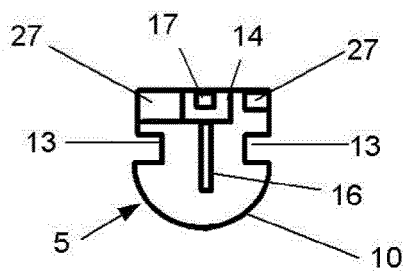
FIG. 10 shows a representation of a carriage along line IX-IX of FIG. 5.

The dynamic stabilizing device 1 includes bone anchoring device 1 includes bone anchoring elements 2 embodied as pedicle screws, which are attached spaced from one another in two bones 3 that are to be stabilized relative to one another, preferably vertebrae. On its ends projecting over the bones 3, the bone anchoring elements 2 are provided with fastening elements 4 for holding an at least partially elastic rod, which is associated with an adjustable device 7 for affecting its elasticity arranged under a coating 6 made from a plastic material, for example a silicone or polyetheretherketone (PEEK). The coating 6 prevents integration of the device 7 after implantation and as a result, permits its adjustability.

The rod 5 has a substantially D-shaped cross section with a flattened side 8, from which legs 9 running parallel to one another extend on both sides, the legs being connected to one another via a curvature 10 opposite the flattened side 8. For forming a section 11 with a greater elasticity relative to the remainder of the rod 5, a cross-sectionally reduced cutout 12 runs from the flattened side 8 also over a central axis of the rod 5 extending in the direction of the curvature 10, whereby the effective cross section of the rod 5 is measured approximately in its center at its most minimal. Guide grooves 13 are formed in the leg 9 of the rod 5 which are oriented parallel to the flattened side 8 and to the longitudinal axis of the rod, which have a length which corresponds at least to the doubled length of the cutout 12, whereby the guide grooves 13 extend on both sides over the center of the rod 5.

In the flattened side 8 of the rod 5, a recess is located, in which an adjusting wheel 14 is inserted, whose upper side 15 runs flush with the flattened side 8 of the rod 5 and on whose lower side, a spindle 16 that is rotatably mounted in the rod 5 is formed. A contact 17 for a tool for turning the adjusting wheel 14 is inset in the upper side 15 of the adjusting wheel 14. The coating 6 has a conical bore 25 for the tool that corresponds to the contact 14. The adjusting wheel 14 has a toothing 18 on its peripheral circumference, which cooperates with a corresponding toothed bar 19 of a carriage 20 displaceable to the adjusting wheel 14.

The carriages 20 which has a substantially U-shaped cross section is mounted to be continuously, variably displaceable on the rod 5 by means of rotation of the adjusting wheel 14, whereby its U-curve 21 corresponds to the curvature 10 of the rod 5 and its U-legs 22 runs parallel to the legs 9 of the rod. The U-legs 22 are provided with guide noses 23, which engage in the guide grooves 13 of the rod 5. On the free ends of the U-legs 22, projections 24 are provided which are aligned to one another, one of which is formed as a toothed bar 19 that cooperates with the adjusting wheel 14. The projects 24 are displaceably mounted in slots 27 in the flattened side 8 of the rod, such that their free upper side runs flush with the flattened side 8 of the rod 5.

In a first end position according to FIGS. 2 and 4, the carriage 5 releases completely the elastic section of the rod 5, that is, it is located completely near the cutout 12 in a region in which the rod 5 has a cross-sectional reduction. Since the reduced cross section of the rod 5 is completely released, the rod has its greatest possible elasticity. Thus, it is already deformable under the effects of relatively minimal forces. In order to reduce the elasticity of the rod 5, that is to increase its rigidity, the carriage is displaced in the direction of the cutout 12 in any desired position, as the adjusting wheel 14 is turned by means of a tool inserted into the contact 17. In this regard, the carriage 20 laterally covers the cutout 12 with its U-legs 22 and supports the rod 5 in the region of its curvature 10. Since the carriage 20 is held via its guide noses 23 and projections 24 on the rod 5, it can counteract corresponding forces or torque which act on the rod 5. After a further shortening of the free length of the elastic section by a corresponding displacement of the carriage 20, this moves into its second end position according to FIGS. 5 and 6, in which it covers the cutout 12 on three sides on its entire length.

If the stabilizing device 1 is implanted and the elasticity of the rod 5 must be changed, it is necessary to rotate the adjusting wheel 14 in the corresponding direction. The rotation can be done, for example, by means of magnetic forces, when the adjusting wheel is made from a corresponding magnetic material or the adjusting wheel 14 is localized, for example by means of an image-guided method and the corresponding position is punctured, in order to guide a tool through the bore 25 of the coating 6 into the contact 17 of the adjusting wheel 14 and in order to rotate the adjusting wheel 14.

Figure 11:
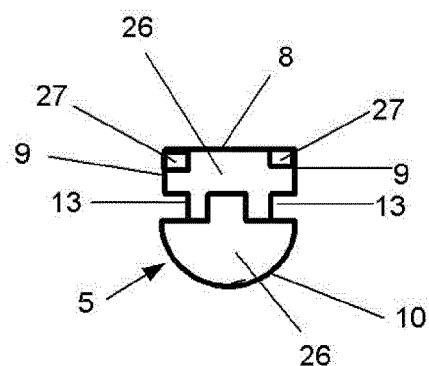
FIG. 11 shows a representation of a carriage along line VIII-VIII of FIG. 5 through a rod in an alternative embodiment.
Figure 12:
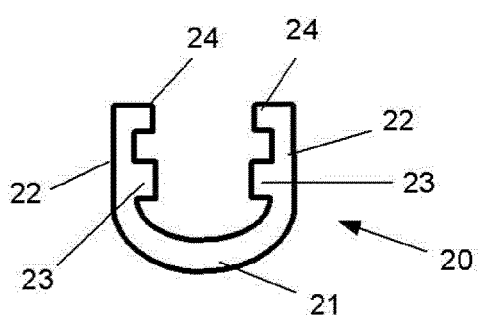
FIG. 12 shows a side view of the carriage.

The rod 5 and the carriage 20 are made from a titanium material. According to FIG. 11, the rod 5 is embodied as two pieces, whereby both parts 26 can be made from different materials, for example, one of the parts 26 made from a titanium material and the other part 26 from a plastic, in particular a polyetheretherketone composite.

REFERENCE NUMERAL LIST 1 stabilizing device
2 bone anchoring element
3 bone
4 fastening element
5 rod
6 coating
7 device
8 side of 5
9 leg of 5
10 curvature of 5
11 elastic section
12 cutout
13 guide groove
14 adjusting wheel
15 upper side
16 spindle
17 contact
18 toothing
19 toothed bar
20 carriage
21 U-bend
22 U-leg
23 guide nose
24 projection
25 bore
26 part of 5
27 slot

I claim:

1. A dynamic stabilizing device (1) for bones (3), comprising:
    two bone anchoring elements (2) spaced from one another;
    at least one rod that is at least partly elastic;
    a plurality of fastening elements (4), wherein said bone anchoring elements (2) are connectable via said fastening elements (4) with said at least one rod (5), wherein the at least one rod (5) has an adjustable device (7) for affecting an elasticity of said rod, wherein the adjustable device (7) is configured to change a free length of an elastic section (11) of the rod (5), wherein said adjustable device (7) comprises a carriage (20) that is moveable over the rod (5) and engages at least in part about the circumference of the rod (5),
    wherein the rod (5) has at least one guide groove (13) that extends parallel to a longitudinal axis of said rod (5), wherein a guide lug (23) of the carriage (20) slidingly engages in said at least one guide groove (13), wherein said guide groove (13) extends over the elastic section (11) coverable by the carriage (20) and has a length, such that the carriage (20) in a first end position releases the elastic section (11), and in a second end position, covers the elastic section (11) over an entire length thereof.

2. The stabilizing device according to claim 1, wherein the adjustable device (7) is adjustable before and/or after implantation of the stabilizing device (1).

3. The stabilizing device according claim 1, wherein the adjustable device (7) has an adjusting wheel (14) for displacing the carriage (20), wherein the adjusting wheel (14) is provided with a contact (17) for a tool and/or is made from a magnetic material, and is rotatably mounted in the rod (5).

4. The stabilizing device according to claim 3, wherein the adjusting wheel (14) has a toothing (18) on at least a part of its outer circumference, which cooperates with a corresponding toothed bar (19) of the carriage that is displaceable to the adjusting wheel (15).

5. The stabilizing device according to claim 1, wherein the rod (5) has a cross sectional narrowing for formation of the elastic section (11) and is coverable by the carriage (20).

6. The stabilizing device according to claim 1, wherein the rod (5) is covered with a coating (6) made from a plastic, leaving projections free for the fastening elements (4).

7. The stabilizing device according to claim 6, wherein the coating (6) has a conical bore (25) on a circumferential side, which runs coaxially to the adjusting wheel (14).

8. The stabilizing device according to claim 6, wherein the coating (6) is made from a silicone or polyetheretherketone (PEEK).

9. The stabilizing device according to claim 1, wherein the rod (5) is made from a titanium material or is formed as two parts in a longitudinal direction, wherein one of the parts (26) is made from a titanium material and the other part (26) is made from a plastic.

10. The stabilizing device according to claim 9, wherein the plastic is a polyetheretherketone composite.

11. The stabilizing device according to claim 1, wherein the carriage (20) is made from a titanium material.

12. The stabilizing device according to claim 1, wherein the coating (6) covers the adjustable device (7) and the elastic section (11) of the rod (5).

13. The stabilizing device according to claim 1, wherein the titanium material of the carriage (2) has a higher rigidity relative to the titanium material of the rod (5).

* * * * *